United States Patent [19]

Legrow et al.

[11] Patent Number: 5,153,268

[45] Date of Patent: Oct. 6, 1992

[54] NAIL LACQUER PRIMARY FILM FORMING RESIN

[75] Inventors: Gary E. Legrow; Milan F. Sojka, both of Midland, Mich.

[73] Assignee: Dow Corning Corporation, Midland, Mich.

[21] Appl. No.: 664,737

[22] Filed: Mar. 5, 1991

[51] Int. Cl.⁵ .............................................. C08F 8/00
[52] U.S. Cl. ................................. 525/288; 525/100; 524/143; 524/279; 524/310; 524/318; 524/315; 524/357; 524/364
[58] Field of Search ................ 525/100, 288; 524/143, 524/279, 310, 318, 315, 357, 364

[56] References Cited

U.S. PATENT DOCUMENTS

| | | | |
|---|---|---|---|
| 3,458,601 | 7/1969 | Johnson et al. | 525/288 |
| 3,650,812 | 3/1972 | Nordstrom et al. | 525/288 |
| 3,706,697 | 12/1972 | Backderf | 525/288 |
| 4,291,136 | 9/1981 | Keogh | 525/288 |
| 4,368,297 | 1/1983 | Kato et al. | 525/100 |
| 4,477,628 | 10/1984 | Kato et al. | 525/100 |
| 4,593,068 | 6/1986 | Hirose et al. | 525/100 |
| 4,683,007 | 7/1987 | Horowitz | 106/308 |

FOREIGN PATENT DOCUMENTS 2-25411  1/1990  Japan.

*Primary Examiner*—John C. Bleutge
*Assistant Examiner*—Karen A. Hellender
*Attorney, Agent, or Firm*—Jim L. DeCesare

[57] ABSTRACT

An improved nail lacquer which includes a film forming resin, a plasticizer and a solvent. The improvement relates to the utilization as the film forming resin of a graft copolymer which has a main backbone chain of acrylic ester monomer units and methacrylic ester monomer units. The main backbone chain has grafted thereto side chain units of carboxyl groups and side chain units of trialkoxysilyl groups. Nail coat compositions containing these film forming resins provide improved wear resistance.

20 Claims, No Drawings

NAIL LACQUER PRIMARY FILM FORMING RESIN

BACKGROUND OF THE INVENTION

This invention relates to a primary film forming resin for nail lacquers and nail enamel formulations and more particularly is directed to a grafted polymeric film forming resin for nail polish which will function as a replacement for nitrocellulose.

Nail lacquers and enamels typically contain several ingredients among which are a primary film former, secondary film formers, plasticizers, solvents, colorants, and fillers. In the past, nitrocellulose has been the primary film former employed in the majority of nail polish formulations but it suffers from the disadvantages that it is explosive; it tends to discolor as a function of time rendering it aesthetically displeasing; and it is prone to undergo sharp changes in viscosity which make application difficult. Thus a need exists in the nail lacquer arts for an improved primary film forming material.

Unlike copolymers having a linear arrangement of sequences such as —AAABBB— and —ABABAB—, graft copolymers are polymers in which the molecules are characterized by a main backbone chain to which side chains containing different atomic constituents are attached at various points along the main chain. For example a graft copolymer can be represented by the structure

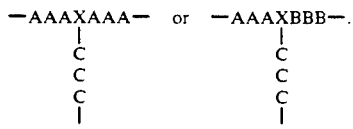

The monomer units A and B are referred to as the main chain or backbone, the sequence of C units is the side chain or graft, and X is the unit in the backbone to which the graft is attached.

Nail lacquers containing graft polymers are not new. U.S. Pat. No. 4,683,007 issued Jul. 28, 1987 discloses a nail polish which includes nitrocellulose grafted to vinyl and acrylic monomers for the purpose of increasing the settling resistance of nitrocellulose. The graft polymers of the present invention however differ from such nitrocellulose grafts in both the main chain units and side chain units employed. In contrast to the '007 patent, the nail lacquer primary film formers of this invention are copolymers in which the main chain includes acrylic ester monomer units and methacrylic ester monomer units, and wherein two differing side chains are grafted to the main chain including both carboxylic acid units and units of trialkoxysily functionality. While Examples 6, 7 and 10 of the '007 patent do not include nitrocellulose, the polymers formed therein contain backbones of all methacrylate units and contain no acrylate units as the polymers of the present invention. Further the polymers of the '007 patent do not include carboxyl units as grafted side chains and where they do include trialkoxysilyl units, the trialkoxysilyl units of the '007 patent are endblocking units rather than side chain grafts. Thus there is a significant difference between the materials of the present invention and the materials of the '007 patent.

Japanese Patent No. 2-25411 dated Jan. 26, 1990 relates to a durable coat cosmetic material including a nail enamel in which a dimethylpolysiloxane compound is copolymerized with acrylate and methacrylate monomers. However a linear polymer instead of a grafted polymer is obtained in which the backbone includes each of acrylate, methacrylate and trialkoxysilyl units. There are also no grafted side chains and no carboxyl unit grafted side chains in distinction to the materials of the present invention. As noted above the copolymeric film formers of the present invention are graft copolymers and not copolymers having linear arrangements of sequences only.

SUMMARY OF THE INVENTION

The invention is directed to a graft copolymer which has a main backbone chain of acrylic ester monomer units and methacrylic ester monomer units. The main backbone chain has grafted thereto side chain units of carboxyl groups and side chain units of trialkoxysilyl groups.

The invention is also directed to a nail lacquer which includes a film forming resin, a plasticizer and a solvent. The improvement in accordance with the present invention relates to the utilization as the film forming resin of the nail lacquer the graft copolymer noted above.

Nail coat compositions containing the novel film forming resins of the present invention have been found to provide improved wear resistance which is a highly desirable and sought after factor in the nail enamel market.

These and other features, objects and advantages of the herein described present invention will become more apparent when considered in light of the following detailed description.

DETAILED DESCRIPTION OF THE INVENTION

Nail lacquer formulations exhibiting improved wear resistance are provided herein by incorporating into nail care compositions as the film forming ingredient a graft copolymer. The graft copolymer in accordance with the present invention includes a main backbone chain of acrylic ester monomer units and methacrylic ester monomer units. In addition the main backbone chain has grafted thereto side chain units of carboxyl groups and side chain units of trialkoxysilyl groups. The graft polymers of the present invention can be represented by the segment structure

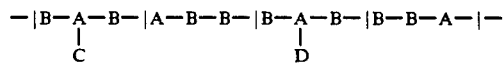

in which A represents an acrylate monomer unit, B represents a methacrylate monomer unit, C represents a carboxyl group and D represents a trialkoxysilyl group.

This random grafted copolymer contains in a typical segment of one hundred A and B units, thirty-three A units and sixty-seven B units. However in such a one hundred unit segment there is only one C unit and one D unit. The C and D units graft to only the A units. In other words, of one hundred "mer" units of the polymer there are sixty-seven B units, thirty-one A units, one A unit that has a C unit grafted thereto, and one A unit that has a D unit grafted thereto. The distribution of the "mer" units is random.

It should be apparent that the polymers of the present invention differ substantially from the materials of the prior art as represented by the aforementioned '007 patent and Japanese patent 25411. For example, the backbone of the polymer of the '007 patent is all B units and does not contain A units. There are no C units in the '007 patent and the D units of the '007 patent are attached to the ends of the backbone rather than being grafted as side chains. Since the polymer of the '007 patent contains no A units, the concept of grafting is absent. As to the Japanese patent 25411, the backbone is a combination of A, B and D units rather than A and B units. There are no C units and no grafted side chains.

The acrylic ester monomer has the formula $CH_2=CHCOOR$ in which R is preferably an alkyl group having from one to sixteen carbon atoms. The methacrylic ester monomer has the formula $CH_2=C(CH_3)COOR'$ in which R' is an preferably an alkyl group having one to fourteen carbon atoms. Most preferred are main backbone chain copolymers in which the acrylic ester monomer is butyl acrylate and the methacrylic ester monomer is methyl methacrylate.

The carboxyl graft is formed by reacting the main backbone chain copolymer with acrylic acid in the presence of a free radical initiator. The trialkoxysilyl graft is formed by reacting the main backbone chain copolymer with an acrylate or a methacrylate functional silane monomer in the presence of a free radical initiator. The grafts are formed by dissolving the main backbone chain copolymer in a solvent and simultaneously reacting the copolymer with acrylic acid and the silane monomer in the presence of a free radical initiator. The silane monomer is preferably 3-methacryloxypropyltrimethoxysilane although there may also be employed methacryloxypropenyltrimethoxysilane, 3-methacryloxypropyltris(methoxyethoxy)silane, and 3-acryloxypropyltrimethoxysilane.

While the most preferred monomers for the backbone chain copolymer are butyl acrylate and methyl methacrylate, other combinations of acrylates and methacrylates may be employed such as methyl, ethyl, propyl, pentyl, hexyl, octyl, nonyl, decyl, dodecyl, tetradecyl and hexadecyl acrylates; and ethyl, propyl, isopropyl, n-butyl, isobutly, sec-butyl, t-butyl, n-hexyl, n-octyl, isooctyl, 2-ethylhexyl, n-decyl and tetradecyl methacrylates.

A particularly distinct advantage of the present invention is that there is produced a material which contains less than about five parts per million of residual monomer. Thus a practically monomer free product is produced by virtue of the fact that any residual monomer is grafted to the polymer. The following is a brief summary of the process for producing the monomer free product including the synthesis of a magnesium hydroxide suspension in which acrylate polymer beads are produced.

Magnesium sulfate is dissolved in water and the solution is reacted with a water solution of sodium hydroxide. This reaction is conducted at a temperature range of twenty to fifty degrees Centigrade while stirring the contents at a rate of 50-1000 rpm. A suspension of two to ten weight percent magnesium hydroxide in water is produced. The reaction is preferably conducted at room temperature at a stirring rate of one hundred rpm, and the concentration of the final suspension is preferably five weight percent. A mixture of hydrolytically stable water insoluble organic arylate monomers together with a free radical initiator are slowly added to the magnesium hydroxide suspension at a temperature of twenty to sixty degrees Centigrade while stirring the contents at a rate of 200-2000 rpm. Acrylate polymer beads are produced with the ratio of polymer beads to magnesium hydroxide being a maximum of four to one. The suspension of polymer beads in water is treated with hydrochloric acid to convert the magnesium hydroxide surface layer on the beads to water soluble magnesium chloride. The beads are separated by filtration, washed and dried. The polymer beads are dissolved in a solvent such as ethyl acetate. Other solvents which may also be employed are set forth below. To the dissolved polymer is added acrylic acid, a free radical initiator and a trialkoxysilyl acrylate monomer. The concentration of acrylic acid and trialkoxysilyl acrylate monomer relative to the polymer is in the range of 0.1-10 percent by weight preferably one percent. The solution is heated for six to twelve hours at fifty to one hundred degrees Centigrade to produce the grafted polymer. Grafting of the monomers to the polymer is complete upon a determination of the presence of no detectable monomer.

The following examples illustrate the present invention and the concepts embodied therewithin.

EXAMPLE I

Into a three neck reaction flask was placed 253.55 grams of $MgSO_4(7H_2O)$ which had been dissolved at room temperature in 391.71 grams of deionized water. While stirring the contents of the flask there was slowly added a solution of 82.3 grams of sodium hydroxide in 678.55 grams of deionized water. The resulting suspension of magnesium hydroxide was purged with nitrogen for ten minutes. The stirring rate in the flask was adjusted to 800 RPM, and in 195 grams of methyl methacrylate and 99 grams of butyl acrylate, 5.88 grams of VAZO 64 initiator were dissolved and added slowly to the suspension. While maintaining a slow nitrogen stream flow, the suspension was heated to sixty degrees Centigrade upon initiation of precipitation of the methyl methacrylate-butyl acrylate polymer beads. After the elapse of two hours the system was heated to eighty degrees Centrigrade for an additional six hours. The flask was allowed to cool to room temperature. The polymer bead suspension was neutralized to a pH of five with hydrochloric acid. Deionized water at fifty degrees Centigrade was used to wash the suspension and establish a neutral pH. The beads were filtered and dried in an oven at about fifty degrees Centigrade. Using a mixer, ninety-eight grams of the beads were dissolved in 900 grams of ethyl acetate. The solution was poured into a three neck reaction flask and purged with nitrogen for ten minutes. While stirring and maintaining a slow nitrogen stream flow, there was added one gram of acrylic acid, one gram of the methacrylate functional silane monomer 3-methacryloxypropyltrimethoxysilane, and two grams of VAZO 64 initiator. The grafted polymer solution in the flask was heated to seventy degrees Centigrade for eight hours. The grafted polymer was free of residual monomer.

EXAMPLE II

Using a mixer, 392 grams of polymer beads formed from the monomers methyl methacrylate, and n-butyl acrylate were dissolved in 600 grams of ethyl acetate. The solution was poured into a three neck reaction flask and purged with nitrogen for ten minutes. While stirring and maintaining a slow nitrogen stream flow, there was added four grams of acrylic acid, four grams of the methacrylate functional silane monomer 3-methacryloxypropyltrimethoxysilane, and eight grams of VAZO 64 initiator. The grafted polymer solution in the flask was heated to seventy degrees Centigrade for eight hours. The grafted polymer was free of residual monomer.

EXAMPLE III

While stirring, there was blended one hundred grams of the grafted polymer solution from Example I and two hundred grams of the grafted polymer solution of Example II. The blended grafted copolymer was found to contain no detectable residual monomer.

EXAMPLE IV

Example I was repeated except that 211.28 grams of magnesium sulfate in crystal form were dissolved in 304.21 grams of deionized water. The amount of sodium hydroxide employed was 68.58 grams in 526.98 grams of deionized water. The resulting grafted polymer contained zero parts per million of free monomer.

EXAMPLE V

Example I was repeated except that the suspension was washed three times with a fifty percent water solution of isopropyl alcohol. The polymer bead to solution ratio was one to thirty. The resulting grafted polymer contained zero parts per million of residual monomer.

EXAMPLE VI

This example is set forth for purpose of comparison. To a three neck reaction flask containing 354.5 grams of ethyl acetate and one gram of VAZO 64 initiator, there was added and dissolved sixty-five grams of methyl methacrylate, thirty-three grams of butyl acrylate, one gram of acrylic acid and one gram of the silane monomer 3-methacryloxypropyltrimethoxysilane. A nitrogen blanket was established and the system was heated to seventy degrees Centigrade for ten hours. The resulting polymer solution was found to contain three hundred parts per million of free monomer.

Nail enamels in accordance with the present invention can be formulated to include the grafted polymers described above as the primary film forming resin. In addition to the primary film forming resin the nail enamels require a plasticizer, a solvent and a colorant.

The plasticizer functions to control the flexibility and the elongation of the film. Plasticizers preferably should be nonvolatile, colorless, odorless and tasteless. Some examples of appropriate plasticizers which may be employed are dibutyl phthalate, tricresyl phosphate, dibutyl phthalate, dibutyl glycolate, dioctyl phthalate, camphor, castor oil, benzyl benzoate, tributyl phosphate, butyl acetal ricenoleate, glyceryl acetal ricenoleate, butyl stearate, tributoxy ethyl phosphate, triphenyl phosphate, triethyl citrate, tributyl citrate, tributyl acetyl citrate, dibutyl tartarate, dimethoxy ethyl phthalate, and diamyl phthalate.

Solvents and diluents which may be used are acetone, ethyl acetate, butyl acetate, methyl glycol acetate, methyl ethyl ketone, methyl isobutyl ketone, methyl acetate, toluene and xylene.

As a colorant there may be employed organic pigments such as The Cosmetics, Toiletries and Fragrance Association designated materials D and C Red Nos. 5-7, 10-13 and 34, and D and C Yellow Nos. 5 and 6. Cosmetic grade inorganic pigments may also be employed such as yellow and red iron oxides, brown iron oxide, iron blue, iron black, carbon black, purified titanium dioxide and bismuth oxychloride.

Nail lacquers and nail enamel formulations in accordance with the present invention contain six to thirty-five percent by weight of the primary film forming resin, five to eight percent by weight of the plasticizer, sixty to eighty percent by weight of the solvent system and about .05 to six percent by weight of colorant.

It will be apparent from the foregoing that many other variations and modifications may be made in the compounds, compositions and methods described herein without departing substantially from the essential features and concepts of the present invention. Accordingly it should be clearly understood that the forms of the invention described herein are exemplary only and are not intended as limitations on the scope of the present invention as defined in the appended claims.

That which is claimed is:

1. A graft copolymer comprising a main backbone chain of acrylic ester units and methacrylic ester units, the main backbone chain having grafted thereto pendant carboxyl groups and pendant trialkoxysilyl groups, the carboxyl grafts being grafted to only acrylic ester units and the trialkoxysilyl grafts being grafted to the remaining unsubstituted acrylic acid ester units.

2. The copolymer of claim 1 in which the acrylic ester unit is formed from a precursor having the formula $CH_2=CHCOOR$ in which R is an alkyl group having from one to sixteen carbon atoms, and the methacrylic ester unit is formed from a precursor having the formula $CH_2=C(CH_3)COOR'$ in which R' is an alkyl group having one to fourteen carbon atoms.

3. The copolymer of claim 2 in which the acrylic ester units are butyl acrylate and the methacrylic ester units are methyl methacrylate.

4. The copolymer of claim 1 in which the carboxyl grafts are formed by reacting the main backbone chain copolymer with acrylic acid in the presence of a free radical initiator.

5. The copolymer of claim 1 in which the trialkoxysilyl grafts are formed by reacting the main backbone chain copolymer with an acrylate or methacrylate functional silane monomer in the presence of a free radical initiator.

6. The copolymer of claim 1 in which the grafts are formed by dissolving the main backbone chain copolymer in a solvent and simultaneously reacting the copolymer with acrylic acid and an acrylate or methacrylate functional silane monomer in the presence of a free radical initiator.

7. The copolymer of claim 6 in which the silane monomer is 3-methacryloxypropyltrimethoxysilane.

8. In a nail lacquer which includes a film forming resin, a plasticizer and a solvent, the improvement comprising utilizing as the film forming resin a graft copolymer with a main backbone chain of acrylic ester units and methacrylic ester units, the main backbone chain having grafted thereto pendant carboxyl groups and pendant trialkoxysilyl groups, the carboxyl grafts being grafted to only acrylic ester units and the trialkoxysilyl grafts being grafted to the remaining unsubstituted acrylic acid ester units.

9. The lacquer of claim 8 in which the acrylic ester unit is formed from a precursor having the formula $CH_2=CHCOOR$ in which R is an alkyl group having from one to sixteen carbon atoms, and the methacrylic ester unit is formed from a precursor having the formula $CH_2=C(CH_3)COOR'$ in which R' is an alkyl group having one to fourteen carbon atoms.

10. The lacquer of claim 9 in which the acrylic ester units are butyl acrylate and the methacrylic ester units are methyl methacrylate.

11. The lacquer of claim 8 in which the grafts are formed by dissolving the main backbone chain copolymer in a solvent and simultaneously reacting the copolymer with acrylic acid and an acrylate or methacrylate functional silane monomer in the presence of a free radical initiator.

12. The lacquer of claim 11 in which the silane monomer is 3-methacryloxypropyltrimethoxysilane.

13. The lacquer of claim 8 which additionally includes a pigment.

14. A method of making a graft copolymer comprising forming a main backbone chain by reacting acrylic ester units and methacrylic ester units, forming a carboxyl graft on the main backbone chain by reacting the main backbone chain with acrylic acid, and forming a trialkoxysilyl graft on the main backbone chain by reacting the main backbone chain with an acrylate or methacrylate functional silane monomer, the carboxyl grafts being grafted to only acrylic ester units and the trialkoxysilyl grafts being grafted to the remaining unsubstituted acrylic acid ester units.

15. The method of claim 14 in which the acrylic ester unit is formed from a precursor having the formula $CH_2=CHCOOR$ in which R is an alkyl group having from one to sixteen carbon atoms, and the methacrylic ester unit is formed from a precursor having the formula $CH_2=C(CH_3)COOR'$ in which R' is an alkyl group having one to fourteen carbon atoms.

16. The method of claim 15 in which the acrylic ester units are butyl acrylate and the methacrylic ester units are methyl methacrylate.

17. The method of claim 14 in which the carboxyl grafts are formed by reacting the main backbone chain copolymer with acrylic acid in the presence of a free radical initiator.

18. The method of claim 14 in which the trialkoxysilyl grafts are formed by reacting the main backbone chain copolymer with an acrylate or methacrylate functional silane monomer in the presence of a free radical initiator.

19. The method of claim 14 in which the grafts are formed by dissolving the main backbone chain copolymer in a solvent and simultaneously reacting the copolymer with acrylic acid and an acrylate or methacrylate functional silane monomer in the presence of a free radical initiator.

20. The method of claim 19 in which the silane monomer is 3-methacryloxypropyltrimethoxysilane.

* * * * *